United States Patent [19]

Zimmerling et al.

[11] Patent Number: 4,961,827

[45] Date of Patent: Oct. 9, 1990

[54] OBTAINING VERY PURE MALEIC ANHYDRIDE FROM CRUDE MALEIC ANHYDRIDE

[75] Inventors: Dieter Zimmerling; Johannes E. Schmidt, both of Ludwigshafen; Rolf Seubert, Frankenthal; Karl Fischer, Hohen-Suelzen; Friedrich Sauer, Obersuelzen, all of Fed. Rep. of Germany

[73] Assignee: BASF Aktiengesellschaft, Ludwigshafen, Fed. Rep. of Germany

[21] Appl. No.: 821,409

[22] Filed: Jan. 22, 1986

[30] Foreign Application Priority Data

Feb. 7, 1985 [DE] Fed. Rep. of Germany ....... 3504146

[51] Int. Cl.$^5$ .............................................. B01D 5/00
[52] U.S. Cl. ...................... 203/87; 203/99; 203/DIG. 19; 549/262
[58] Field of Search ............ 203/87, 91, 99, DIG. 19; 202/198, 179; 549/203, 262, 233; 55/80

[56] References Cited

U.S. PATENT DOCUMENTS

| | | | |
|---|---|---|---|
| 2,670,355 | 2/1954 | Barsky et al. | 203/87 |
| 3,054,806 | 9/1962 | Feder | 549/26.2 |
| 3,401,096 | 9/1968 | Wondrak | 203/87 |
| 3,420,750 | 1/1969 | Schaefer et al. | 202/236 |
| 3,476,775 | 11/1969 | Sueur | 203/87 |
| 3,534,562 | 10/1970 | Thijssen | 203/87 |
| 3,540,987 | 11/1970 | Garkish et al. | 203/DIG. 19 |
| 3,564,022 | 2/1971 | Manoff | 549/203 |
| 3,622,600 | 0/1971 | Feder | 549/203 |
| 3,725,211 | 4/1973 | Gehrken et al. | 203/99 |
| 3,818,680 | 6/1974 | Marquis | 55/48 |
| 3,939,183 | 2/1976 | Gardner | 549/262 |
| 3,965,123 | 6/1976 | Franklin | 549/262 |
| 3,965,126 | 6/1976 | Wirth et al. | 549/262 |
| 4,233,267 | 11/1980 | Coker et al. | 203/87 |
| 4,260,546 | 4/1981 | Schroeder et al. | 549/262 |
| 4,364,748 | 12/1982 | Bakshi | 549/262 |

FOREIGN PATENT DOCUMENTS

| | | | |
|---|---|---|---|
| 0570371 | 8/1977 | U.S.S.R. | 203/DIG. 19 |
| 0822612 | 10/1959 | United Kingdom | 549/262 |
| 0969283 | 9/1964 | United Kingdom | 549/262 |
| 0993712 | 6/1965 | United Kingdom | 549/262 |
| 1204846 | 9/1970 | United Kingdom . | |
| 1291354 | 10/1972 | United Kingdom . | |

*Primary Examiner*—Virginia Manoharan
*Attorney, Agent, or Firm*—John H. Shurtleff

[57] ABSTRACT

Very pure maleic anhydride having a stable color is obtained by fractional distillation of crude maleic anhydride by a method in which the maleic anhydride vapor separated off from low boilers and high boilers is partially condensed so that from 0.5 to 15% by weight of the maleic anydride vapor is separated off from the vapor phase as a liquid precondensate, and the remaining very pure maleic anhydride vapor is then completely condensed.

4 Claims, No Drawings

OBTAINING VERY PURE MALEIC ANHYDRIDE FROM CRUDE MALEIC ANHYDRIDE

The present invention relates to a process for obtaining very pure maleic anhydride from crude maleic anhydride by fractional distillation.

It is known that maleic anhydride is prepared by catalytic vapor-phase oxidation of benzene, naphthenes, butenes and butane. It is also obtained as a by-product in the preparation of phthalic anhydride by oxidation of o-xylene or naphthalene. It is isolated from the crude maleic anhydride, usually by fractional distillation, in which it is obtained in the form of white, virtually pure maleic anhydride.

One well known process employing such a fractional distillation is that disclosed in British Pat. No. 1,291,354 wherein in distillation of the crude maleic anhydride is carried out in a column at a temperature of from 100° to 180° C. and a pressure of from 50 to 300 mm Hg. The base of the column is connected to a circulation evaporator. The pure vaporous maleic anhydride is withdrawn from the middle portion of the column, and the low-boiling portions are driven off at the top. The non-volatile or difficulty volatile compounds are continuously centrifuged out of the base.

However, we have found that the "pure" white maleic anhydride thus obtained tends to become discolored on prolonged standing. Discoloration takes place even more rapidly when the maleic anhydride is kept in the molten state. Since such discoloration is sometimes very troublesome when the maleic anhydride is used further, especially when it is used for the preparation of, for example, polyester resins and alkyd resins, one of the proposals made has been to convert maleic anhydride which does not have a stable color to very pure maleic anhydride having a stable color by a chemical treatment. Thus, according to British Pat. No. 1,204,846, for example, dibenzyl sulfide is added to the distilled maleic anhydride. German Laid Open Application DOS No. 2,008,619 discloses that a product having a stable color is obtained if liquid maleic anhydride is passed over a bed of certain inorganic salts, such as barium chloride.

The treatment of maleic anhydride with chemical additives is technically complicated and moreover has the disadvantage that further impurities are introduced into the maleic anhydride. Hence, a process was sought which makes it possible to obtain very pure maleic anhydride having a stable color without chemical treatment.

We have found that very pure maleic anhydride which has a stable color and a long shelf life is obtained in the preparation of maleic anhydride by fractional distillation of crude maleic anhydride if the maleic anhydride vapor separated off from low boilers and high boilers is partially condensed so that from 0.5 to 15% by weight of the maleic anhydride vapor is separated off from the vapor phase as a liquid precondensate, and the remaining very pure maleic anhydride vapor is then completely condensed.

The novel process starts from a maleic anhydride obtained in a conventional manner, for example by catalytic oxidation of benzene, naphthenes, phenol, furan, but-1-ene, but-2-ene, butane, o-xylene or naphthalene. The crude maleic anhydride obtained by one of these syntheses is subjected to conventional fractional distillation, which may be carried out either continuously or batchwise.

In this distillation to effect purification, low boilers and high boilers are separated off from the crude maleic anhydride, while the maleic anhydride to be isolated is removed as a vapor fraction containing not less than 98% by weight of maleic anhydride. The step according to the invention comprises partially condensing the maleic anhydride vapor, which is substantially pure but does not have a stable color, so that initially from 0.5 to 15, and preferably from 0.5 to 10, % by weight of the vapor fraction is separated off in liquid form, and condensing the remaining vapor to give very pure maleic anhydride having a stable color.

To carry out the partial condensation of the vapor fraction, for example, the vapor stream is passed through a condenser, and the temperature is controlled so that the desired fraction of the maleic anhydride vapor condenses and can therefore be separated off from the vapor stream in liquid form as a precondensate. After the precondensate has been separated off, the vapor stream consists of very pure maleic anhydride having a stable color, and can then be completely condensed in a conventional manner.

The novel process can be carried out downstream of the conventional distillation of crude maleic anhydride.

In a continuous procedure, for example, a crude maleic anhydride which contains, for example, not more than 25% by weight of impurities such as maleic acid, citraconic acid, phthalic acid or their anhydrides and benzoic acid and other impurities is distilled in a distillation column equipped with trays so that low boilers are removed at the top and high boilers are removed as a bottom product. The maleic anhydride substantially freed from the by-products in this manner is taken off as a side stream of the column, in vapor form. It has a purity of not less than 98% by weight. To effect partial condensation, this maleic anhydride vapor is passed through, for example, a coil condenser in which the partial condensation is controlled by regulating the temperature of the cooling medium so that the required amount of precondensate can be separated off from the maleic anhydride vapor. The remaining maleic anhydride vapor is recovered after this partial condensation by complete condensation.

The novel process gives a very pure maleic anhydride which has a stable color, a purity greater than 98% by weight and a Hazen color number of less than 40 on heating. The long shelf life of the maleic anhydride prepared in this manner and stored in liquid form is evident from the fact that the color number on heating does not change even after storage for from 6 to 8 weeks.

It is surprising that, by separating off, by partial condensation, such a small part of the maleic anhydride obtained by fractional distillation, the by-products responsible for the troublesome darkening of the pure material can be removed so substantially that such a high quality maleic anhydride is obtained.

EXAMPLE 623 g/h of a crude maleic anhydride composed of 81% by weight of maleic anhydride, 6% by weight of maleic acid, 4% by weight of citraconic acid, 4% by weight of phthalic acid, 4% by weight of benzoic acid and 1% by weight of other impurities were introduced continuously at the 18th bubble cap tray of a glass column, at a feed temperature of 100° C. The column had a diameter of 80 mm, contained 60 bubble cap trays and was operated under a pressure of 150 mbar at the top.

A total amount of distillate of 1928 g/h (condensation temperature 138° C.) was measured at the top of the column, 10 g/h being removed as a top product and 1918 g/h being recycled to the top of the column. The top product was composed of 271 ppm by weight of citraconic anhydride and 99.97% by weight of maleic anhydride. The top product was not analyzed for water.

100 g/h of bottom product (temperature 163° C.) were removed from the column. The material removed from the bottom contained 19% by weight of maleic anhydride, 25% by weight of benzoic acid, 25% by weight of phthalic anhydride and other impurities, such as high boiling hydrocarbons, high molecular weight organic acids and decomposition products. 503 g/h of maleic anhydride vapor were taken off at the 50th bubble cap tray, at a temperature of 139° C. It was composed of 99.7% by weight of maleic anhydride and 0.3% by weight of citraconic anhydride. The maleic anhydride vapor was passed into a small upright glass condenser. The cooling medium used was Marlotherm. The temperature of the cooling medium was adjusted so that 2% of the amount of gas, corresponding to 10 g/h, were condensed as a precondensate. The condensation temperature was 138.5° C. The remaining 503 g/h of maleic anhydride vapor were completely condensed in a downstream glass condenser. After being completely condensed, the temperature of the maleic anhydride was still 75° C.

The color number on heating was determined for both the maleic anhydride obtained as a precondensate and the pure maleic anhydride obtained as a condensate in the total condensation. The following values were obtained:

|  | Color number on heating (Hazen units) after a storage time of | | | | |
|---|---|---|---|---|---|
|  | 0 | 2 weeks | 4 weeks | 6 weeks | 8 weeks |
| 1. Precondensate | >200 | >200 | >200 | >200 | >200 |
| 2. Condensate 2% by weight | <40 | <40 | <40 | <40 | <40 |

-continued

|  | Color number on heating (Hazen units) after a storage time of | | | | |
|---|---|---|---|---|---|
|  | 0 | 2 weeks | 4 weeks | 6 weeks | 8 weeks |
| 3. Condensate 6% by weight | <40 | <40 | <40 | <40 | <40 |
| 4. Condensate 10% by weight | <40 | <40 | <40 | <40 | <40 |

In tests 2 to 4, the pure maleic anhydride obtained by total condensation after from 2 to 10% by weight, based on the maleic anhydride vapor removed from the sidestream of the column, of precondensate had been separated off was investigated. To determine the color number on heating, or the heat stability, the sample was heated at 140° C. for 2 hours in a test tube and then compared with the Hazen scale.

We claim:

1. In a process for the fractional distillation of a crude maleic anhydride in a column wherein the low boiling impurities are removed from the top of the column, the high boiling impurities are removed from the bottom of the column, and a purified maleic anhydride is withdrawn from the middle of the column as a vapor stream containing not less than 98% by weight of maleic anhydride, the method of improving the purity and color stability of the withdrawn maleic anhydride which comprises:

partially condensing the withdrawn vapor stream of maleic anhydride such that about 0.5 to 15% by weight of said vapor stream is condensed and separated from the vapor phase as a liquid precondensate, and then condensing the remaining portion of said vapor stream to recover a maleic anhydride of improved purity and color stability.

2. A process as claimed in claim 1 wherein the partial condensation step is carried out to condense and separate off about 0.5 to 10% by weight of the maleic anhydride vapor stream as the liquid precondensate.

3. A process as claimed in claim 1 wherein the fractional distillation is carried out continuously.

4. A process as claimed in claim 1 wherein the crude maleic anhydride to be purified is obtained by catalytic oxidation of a compound selected from the group consisting of benzene, naphthenes, phenol, furan, but-1-ene, but-2-ene, butane, o-xylene and naphthalene.

* * * * *